United States Patent [19]
Deutsch

[11] Patent Number: 5,209,227
[45] Date of Patent: May 11, 1993

[54] THERMOELECTRIC THERAPY DEVICE AND MOISTURIZING DEVICE THEREFOR

[76] Inventor: Richard Deutsch, 8 Bayview Ave., Islip, N.Y. 11751

[21] Appl. No.: 815,958

[22] Filed: Jan. 2, 1992

Related U.S. Application Data

[63] Continuation-in-part of Ser. No. 587,407, Sep. 25, 1990, Pat. No. 5,097,828.

[51] Int. Cl.⁵ .............................................. A61F 7/00
[52] U.S. Cl. ..................................................... 128/399
[58] Field of Search ........................... 128/399, 400

[56] References Cited

U.S. PATENT DOCUMENTS

| | | | |
|---|---|---|---|
| 1,480,353 | 1/1924 | Wappler | 128/800 |
| 1,653,901 | 12/1927 | Haessly | 128/399 X |
| 3,133,539 | 5/1964 | Eidus | 128/399 |
| 3,168,895 | 2/1965 | Okuhara | 128/399 |
| 3,207,159 | 9/1965 | Tateisi | 128/399 |
| 4,585,002 | 4/1986 | Kissin | 128/399 |
| 4,640,284 | 2/1987 | Ruderian | 128/399 |
| 4,860,748 | 8/1989 | Chiurco et al. | 128/399 |
| 4,915,108 | 4/1990 | Sun | 128/399 X |

*Primary Examiner*—William H. Grieb
*Attorney, Agent, or Firm*—Hoffmann & Baron

[57] ABSTRACT

A device is provided for heating and moisturizing the skin. The device includes a handle and a thermally conductive head secured to the handle. The head includes a thermally conductive contact plate which is thermally isolated from the head. One or more Peltier effect devices are provided for heating or cooling the contact plate depending upon the polarity of the current. The head and handle function as a heat sink for dissipating heat generated by the Peltier effect devices. A fan is also provided within the head for heat dissipation purposes. A reservoir filled with a moisturizing liquid is mounted to the head and positioned adjacent to the contact plate. The reservoir includes a permeable wall which conforms to the surface of the body to which it is applied.

20 Claims, 5 Drawing Sheets

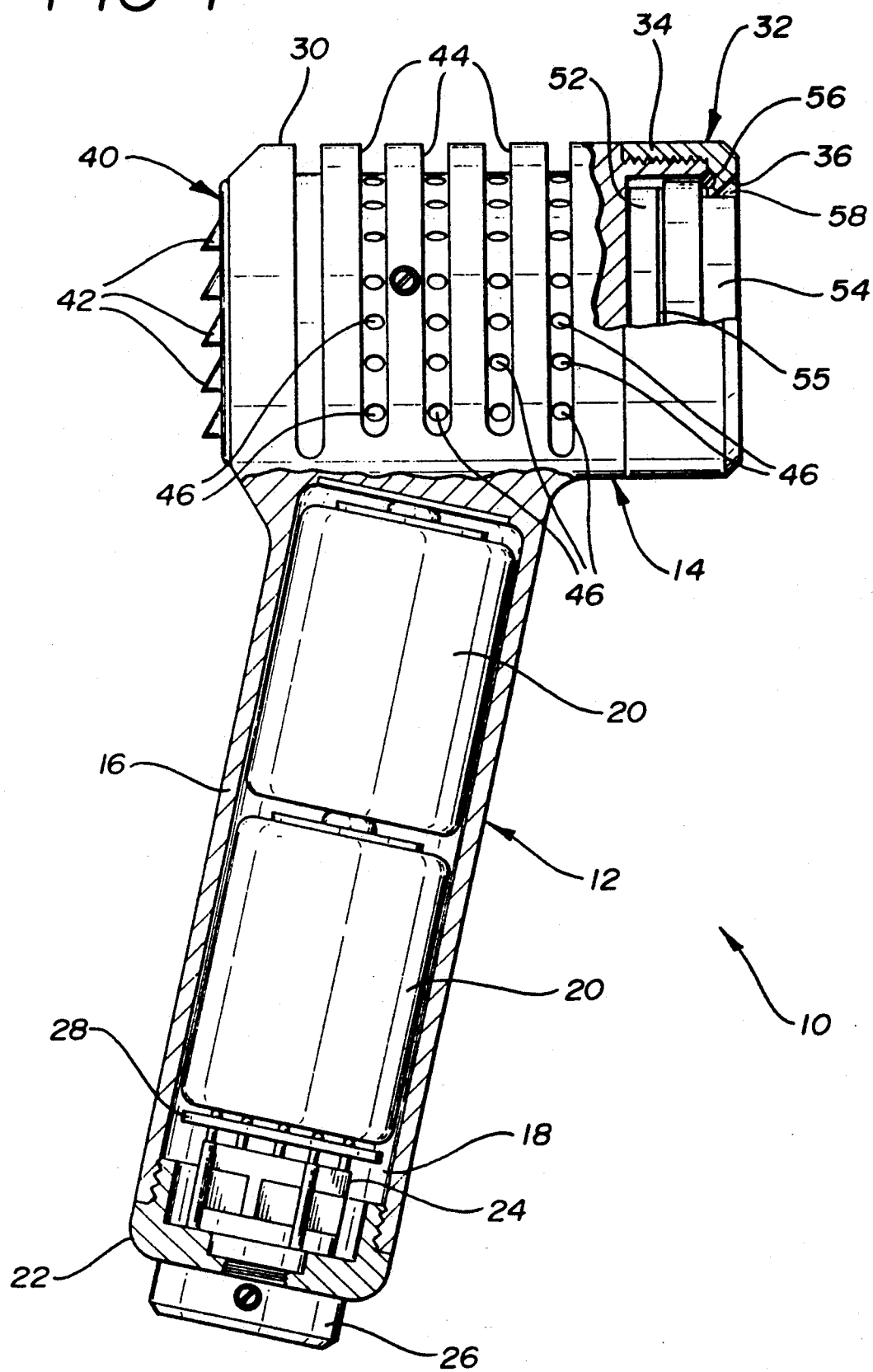

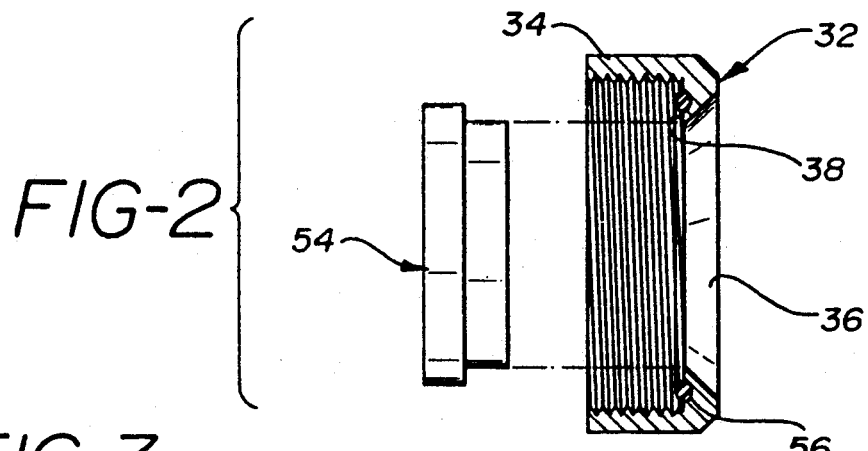
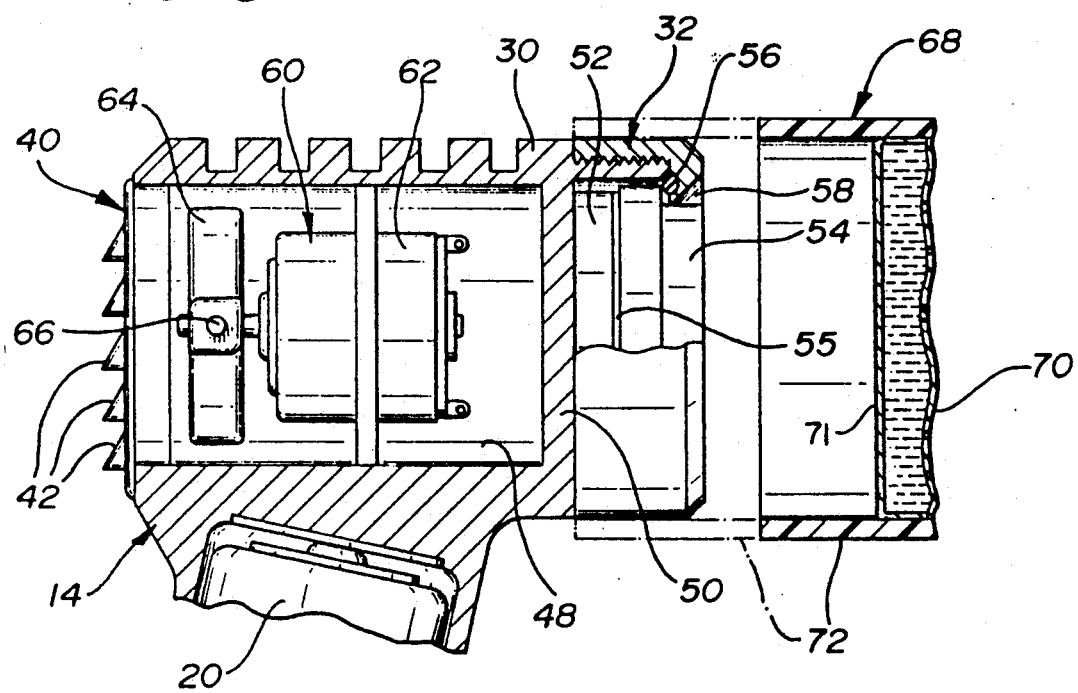
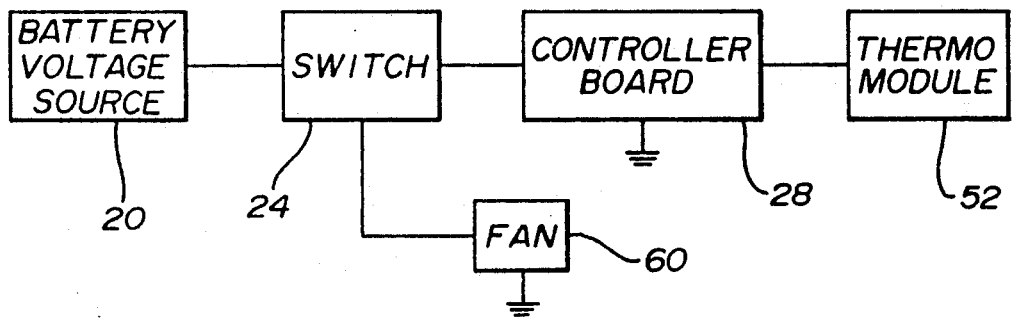

THERMOELECTRIC THERAPY DEVICE AND MOISTURIZING DEVICE THEREFOR

CROSS REFERENCE TO RELATED APPLICATION

This is a continuation-in-part of U.S. application Ser. No. 07/587,407 filed Sep. 25, 1990, now U.S. Pat. No. 5,097,828.

BACKGROUND OF THE INVENTION

1. Field of the Invention

The field of the invention relates to devices for heating, cooling and moisturizing the surface of the body.

2. Brief Description of the Prior Art

The use of heat, cold and moisture for therapeutic purposes is well known. Hot water bags, ice packs, and the like have commonly been used to alleviate pain, to stimulate the flow of blood, or to restrict the flow of blood beneath the surface of the skin. Vaporizers, steamers and the like have been used to moisturize the skin. One of the problems with hot water bags is that the temperature steadily decreases during use, thereby necessitating refilling them with a heated liquid. Ice packs steadily increase in temperature when applied to the skin, and ice must accordingly be added from time to time if a cold temperature is to be maintained. It is also difficult to regulate the temperature of an ice pack or a hot water bottle such that it is neither too cold nor too hot when applied to the skin.

A number of therapeutic devices have been developed which employ Peltier thermoelectric units for providing heat or cold. Such devices include switches which allow reversing the polarity of the current passing through the thermoelectric units, thereby determining whether a hot or a cold stimulus is to be applied thereby. U.S. Pat. No. 3,207,159 discloses such a device which includes a probe for heating or cooling selected cutaneous points. U.S. Pat. Nos. 4,585,002 and 4,860,748 disclose devices which employ microprocessors for controlling the duration and/or intensity of heat and cold generated by Peltier thermoelectric units. U.S. Pat. Nos. 3,133,539, 3,168,895, 4,640,284 and 4,915,108 disclose various other therapeutic devices for applying heat or cold to the skin.

In addition to steamers of the type including an open-ended reservoir, absorbent pads have been secured to electric heating devices in order to allow a person to heat and/or moisturize the skin. U.S. Pat. No. 1,653,901 discloses one such device.

SUMMARY OF THE INVENTION

It is an object of the invention to provide a therapeutic device for applying heat, cold or moisture to the skin.

It is another object of the invention to provide a device which can selectively apply moisture to the skin in a controlled manner.

A still further object of the invention is to provide a moisturizing device which is easily securable to or removable from a therapeutic heating device.

In accordance with these and other objects of the invention, a device is provided for moisturizing the skin which includes a housing, the housing including a handle portion to allow the device to be easily held and manipulated using one hand. A heat source is mounted to the housing. A liquid-filled reservoir is secured to the housing, and preferably removably secured thereto. The reservoir includes a wall having a substantially impermeable portion. The heat source is positioned in proximity to the reservoir in order to heat the liquid as the flexible, permeable wall of the reservoir is applied to the skin. The reservoir is filled prior to mounting it to the housing by a process other than dipping it within a liquid container. A cover is preferably provided for protecting against leakage through the permeable wall and evaporation until the device is readied for use.

In accordance with a further embodiment of the invention, a moisturizing device is provided which includes a rigid sleeve, one end of which is adapted to be secured to a heating device, the other end of which has a reservoir mounted thereto. The reservoir includes a wall having a substantially impermeable portion and a flexible, permeable portion which is used for engaging the skin. The permeable portion of the wall extends outside the sleeve.

BRIEF DESCRIPTION OF THE DRAWINGS

FIG. 1 is a partially sectional, elevation view of a thermoelectric therapy device in accordance with the invention;

FIG. 2 is an exploded, side elevation view of a face cap and contact plate used within the device;

FIG. 3 is a sectional, elevation view of the head of the device having a moisturizing device according to one embodiment of the invention;

FIG. 4 is a schematical illustration of the electrical circuit employed within the device;

DETAILED DESCRIPTION OF THE INVENTION

Figure 5:
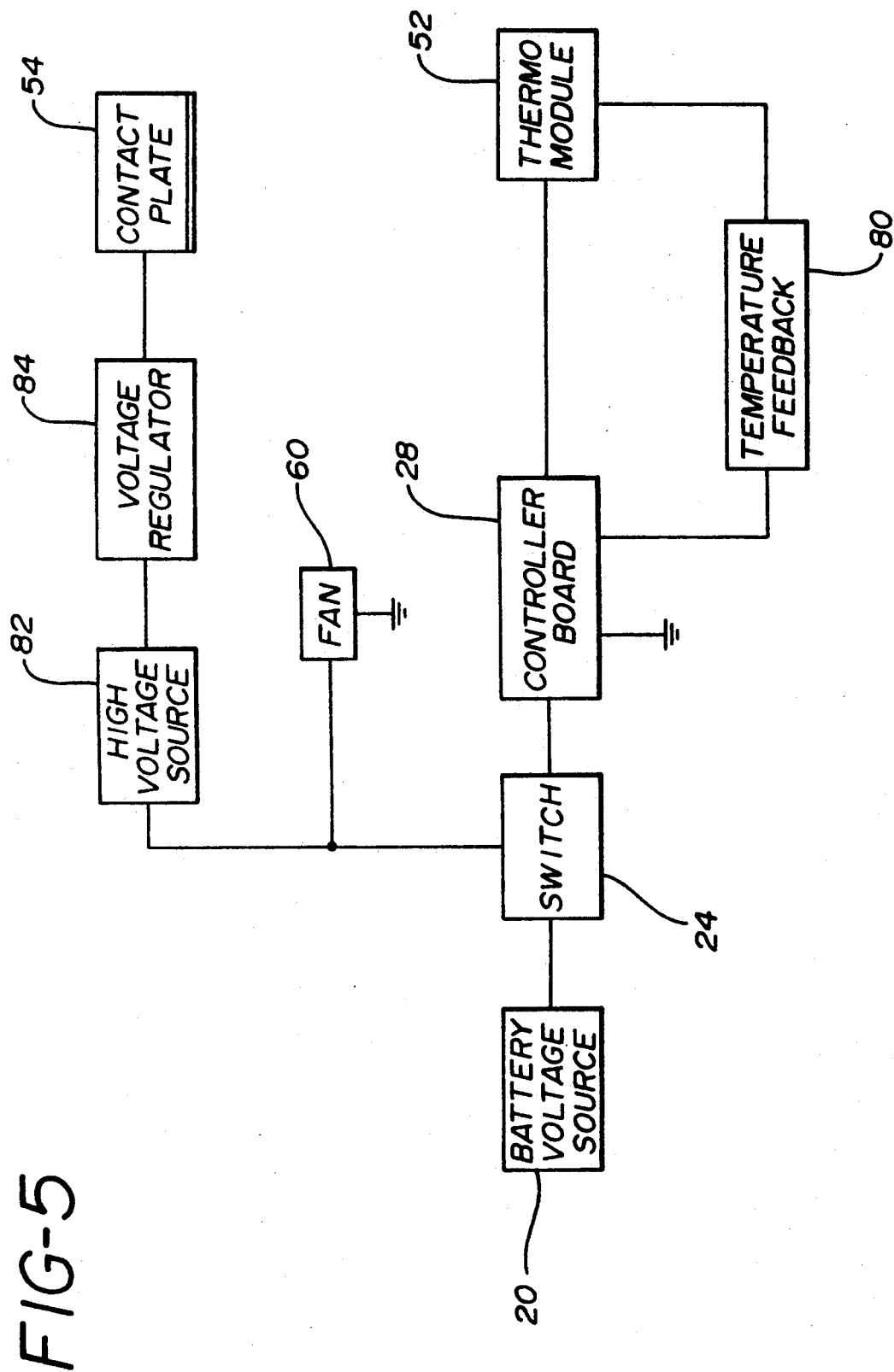
FIG. 5 is a schematical illustration of an alternative electrical circuit employed within the device.

A therapy device 10 as shown in FIG. 1 is provided. The device includes a substantially cylindrical handle 12 and a substantially cylindrical head 14. The handle and head are preferably of integral construction, and are made from a thermally conductive material such as aluminum, copper, or an alloy containing both of these metals and silicon.

The handle includes a cylindrical wall 16 which defines an enclosure 18. The enclosure is adapted for receiving at least one battery. Two rechargeable, nickel-cadmium batteries 20 are positioned within the enclosure shown in FIG. 1. Other types of batteries may alternatively be employed.

A tail cap 22 is threadably secured to the end of the handle 12 opposite from the head 14. A three-way switch 24 is positioned within the enclosure 18 and adjacent to the tail cap. A knob 26 extending outside the tail cap controls the operation of the switch. The opposite end of the switch is connected to a controller board 28.

Referring now to FIGS. 1–3, the head 14 includes a substantially cylindrical wall 30 having an opening at its front end and an opening at its rear end. A face cap 32 is threadably secured to the front end of the head. The face cap includes an annular body 34 having a bevelled front wall 36. A shoulder 38 is defined by the rear surface of the front wall, as best shown in FIG. 2.

A vented plate 40 including fins 42 is secured to the rear end of the head. A plurality of grooves 44 are defined in the outer surface of the cylindrical wall 30. The grooves 44 extend circumferentially about the axis of the head. Alternatively, the grooves may extend axially. Vent openings 46 extend through the cylindrical wall 30 at the grooved portions thereof.

The cylindrical wall 30 defines a chamber 48. The vented plate 40 defines one end of the chamber while a front wall 50 defines the opposite end thereof. A thermo module 52 adjoins the front side of the front wall. The thermo module includes thermoelectric means including a Peltier effect device. A hat-shaped, thermally conductive contact plate 54 adjoins the thermo module. A thin, ceramic insulator 55 is positioned between the thermo module 52 and contact plate 54, thereby electrically insulating the latter. The contact plate is thermally isolated from the face cap 32, which maintains it in position, by an O-ring 56. The face cap may alternatively be made from plastic to provide such thermal insulation. An annular space 58 defined between the inner surface of the end cap and the edge of the contact plate also provides thermal isolation. The O-ring is slightly compressed between the shoulder 38 of the face cap and a shoulder defined by the hat-shaped contact plate. The contact plate accordingly does not tend to move axially or laterally with respect to the head 14.

A fan 60 is mounted within the chamber 48, as shown in FIG. 3. Other equivalent means for circulating air could alternatively be employed. The fan includes a motor 62 having a blade 64 secured thereto. The blade is positioned adjacent to the vented plate 40. A weight 66 may be added to one of the fan blades to cause the head to vibrate slightly when the fan is operated.

A fluid-filled end piece 68 may be mounted to the front end of the head 14 as shown in dotted lines in FIG. 3. The end piece includes a reservoir having a permeable membrane or wall 70 and a rigid, impermeable container 71 which is secured to an elastic sleeve 72. The permeable wall 70 conforms to the surface of the skin to which it is applied. It is either heated or cooled depending upon the temperature of the adjoining contact plate. The sleeve is preferably substantially non-conductive of heat, while the rigid container portion of the reservoir may be made from a metal which is highly heat-conductive. The container may either be slidably positioned within the sleeve so that it moves towards the end of the sleeve when the sleeve is secured to the head, or fixedly secured to one end of the sleeve. The reservoir preferably includes no absorbent materials, and is not intended to be filled by dipping it into a container of moisturizing liquid.

Figure 6:
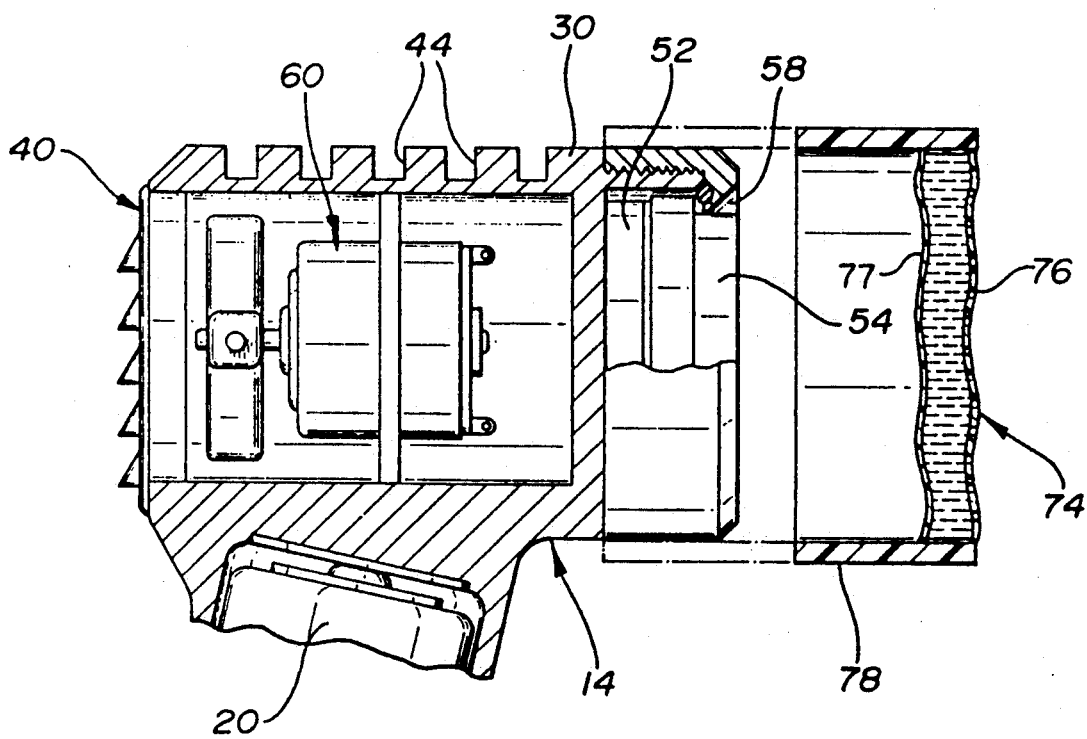
FIG. 6 is a sectional view of a porous pouch secured to the front end of the head of the device.

In an alternative embodiment of the invention shown in FIG. 6, a reservoir in the form of a fluid-filled bag 74 having a flexible porous wall 76 is secured to the front end of the head by a rigid sleeve 78. The sleeve 78 is frictionally engageable with the outer surface of the head 14. Moist heat may be accordingly provided by the device 10 when fitted with such a bag as the flexible, impermeable wall portions 77 of the bag readily conduct heat.

FIG. 4 provides a schematical illustration of one electrical circuit which may be used within the device 10. An alternative circuit is shown in FIG. 5. This circuit includes the same elements shown in FIG. 4, plus a temperature feedback loop 80, a high voltage source 82, and a voltage regulator 84. The temperature feedback loop allows the temperature of the thermo module, and therefore the contact plate, to be maintained within preselected limits. In addition, the temperature may be varied as a function of time between hot and cold.

Electrical stimulation of the skin and underlying muscles may be provided through the use of the high voltage source and the voltage regulator. The high voltage source may be a multi-vibratory transformer circuit or the like. A polarity switch (not shown) may also be employed in this loop. The switch controls the direction of the current and, therefore, the type of electrical therapy provided (i.e. desensitization (sedation) or stimulation (tetenization)).

In operation, the device is used for applying heat or cold to a relatively large, circular area defined by the outer surface of the contact plate 54. The knob 26 is turned to actuate the switch 24. Current flows in a selected direction through the thermo module 52, thereby causing it to heat or cool the contact plate 54. The fan is simultaneously actuated, and helps maintain the thermal gradient across the thermo module and the device itself.

The relative surface areas and masses of the thermo module, contact plate, head 14 and handle 12 are such that excess heat which may be generated by the thermo module is easily absorbed by the head and handle. The head and handle, each being thermally conductive and having much larger masses and surface areas than the contact plate, function as a large heat sink which easily dissipates such heat. The fan, grooves and vent openings are also strategically positioned to efficiently circulate and exhaust air within the chamber 48. There is accordingly no danger of thermal runaway regardless of how long the device is operated.

The knob 26 is turned to a different position if one desires to reverse the current flow through the thermo module. The fan is actuated regardless of the direction of current flow through the thermo module.

If one desires to apply moist heat to the skin, a prefilled reservoir may be mounted to the front end of the head as shown in FIGS. 3 and 6. The size of the pores in the permeable walls is exaggerated in these figures for illustrative purposes. Such pores may simply be pinholes in a material such as latex. Alternatively, the walls may simply be membranes which are sufficiently permeable to allow the slow passage of the liquid within the reservoir to pass therethrough. The permeability required will depend upon the particular liquid contained within the reservoir. Liquid within the pouch can slowly escape as the pouch is applied to the skin. The knob 26 is turned in the appropriate direction so that heat is applied to the contact plate and, in turn, the impermeable wall of the reservoir and liquid therein. The term "liquid" as employed herein encompasses liquid materials as well as suspensions, colloids and other such materials which may be used for moisturizing the skin.

Figure 7:
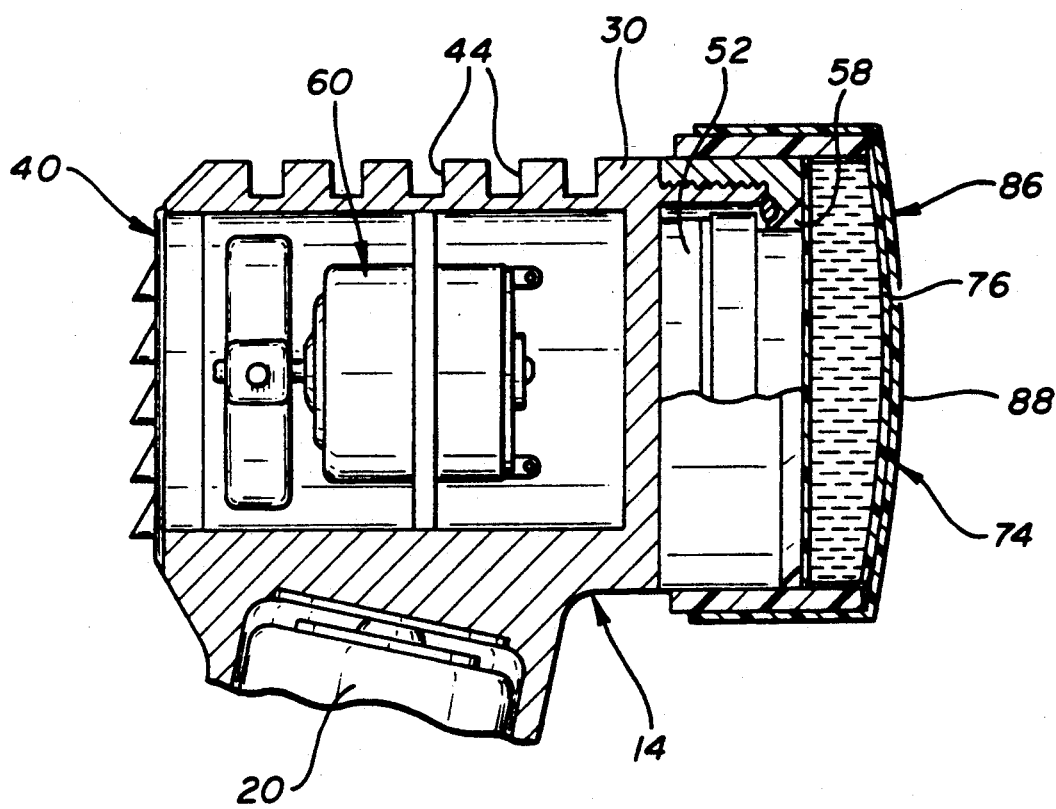
FIG. 7 is a sectional view showing a moisturizing device and cover secured to the front end of the head of the therapy device.

As shown in FIG. 7, the permeable wall 76 of the fluid-filled bag 74 is preferably protected by a cover 86 when not applied to the skin. The cover 86 is removably secured to the sleeve 78 in such a manner that the liquid does not evaporate from or leak out from the permeable wall 76 of the bag 74. The front wall 88 of the cover preferably engages the permeable wall 76 when secured to the sleeve. The permeable wall 76 extends beyond the end of the sleeve to permit its engagement with the cover 86 or the skin. The front wall 88 of the cover may be flexible or semi-rigid.

A gentle vibratory motion is imparted by the device 10 due to the eccentric weighing of the fan blade 64. Such vibration can alternatively be provided by a mechanical vibrator.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention. The heat source may, for example, be a resistive heat source positioned within the reservoir rather than adjacent thereto. The reservoir, while preferably removable from the heating device, may be integrally formed therewith if an inexpensive heat source is employed. The entire heating and moisturizing assembly would then simply be discarded once all of the moisturizing liquid has been used.

What is claimed is:

1. A device for moisturizing the skin, comprising:
   a housing, said housing including a handle portion;
   a heat source mounted to said housing;
   a pre-filled, liquid-containing, integral reservoir including a wall having a substantially impermeable portion which does not permit liquid to pass therethrough and a flexible permeable portion which allows the passage of liquid slowly therethrough, said heat source being positioned in proximity to said reservoir and capable of heating the liquid within said reservoir, and
   means for removably securing said reservoir to said housing.

2. A device as described in claim 1, including a substantially impermeable cover which covers at least said permeable portion of said wall of said reservoir.

3. A device as described in claim 2, including means for removably securing said cover to said reservoir.

4. A device as described in claim 3, wherein said cover includes a portion which engages at least the permeable portion of said wall of said reservoir.

5. A device as described in claim 1, wherein said means for securing said reservoir includes a sleeve, said sleeve being coupled to said housing.

6. A device as described in claim 5, wherein said sleeve is substantially rigid.

7. A device as described in claim 6, wherein said sleeve includes a first end portion and a second end portion, said first end portion including means for removably securing said sleeve to said housing, said second end portion being secured to said wall of said reservoir in such a manner that said permeable portion of said wall of said reservoir extends outside said sleeve.

8. A device as described in claim 7, including a substantially impermeable cover which covers at least said permeable portion of said wall of said reservoir.

9. A device as described in claim 8, wherein said cover is removably secured to said sleeve.

10. A device as described in claim 7, wherein said housing includes a heat conductive contact plate, said sleeve being positionable upon said housing such that said impermeable portion of said wall of said reservoir engages said contact plate, said heat source being in close proximity to said contact plate.

11. A device as described in claim 10, wherein said sleeve is substantially non-conductive of heat.

12. A device as described in claim 1, wherein said reservoir contains substantially no absorbent materials within said wall.

13. A device as described in claim 1, wherein said impermeable portion of said wall of said reservoir is flexible.

14. A moisturizing device for use with a heating device, comprising:
    a rigid sleeve including a first end portion and a second end portion, said first end portion being adapted to be secured to a heating device; and
    a reservoir including a wall having a substantially impermeable portion and a flexible, permeable portion which allows the passage of liquid slowly therethrough, said reservoir being secured to said second end portion of sleeve such that said permeable portion extends outside said sleeve and said impermeable portion extends at least partially within said sleeve.

15. A device as described in claim 14, wherein said sleeve is substantially non-conductive of heat.

16. A device as described in claim 14, wherein said impermeable portion of said wall of said reservoir is heat conductive.

17. A device as described in claim 16, wherein said reservoir contains substantially no absorbent materials within said wall.

18. A device as described in claim 17, wherein said impermeable portion of said wall of said reservoir is flexible and said permeable portion is made from a non-absorbent material.

19. A device for moisturizing the skin, comprising:
    a housing said housing including a handle portion;
    a heat source mounted to said housing; and
    a pre-filled, liquid-containing, integral reservoir including a wall having a substantially impermeable portion which does not permit liquid to pass therethrough and a flexible, permeable portion which allows the passage of liquid slowly therethrough, said permeable portion being made from a non-absorbent material having a plurality of small openings extending therethrough, said heat source being positioned in proximity to said reservoir and capable of heating the liquid within said reservoir.

20. A device as described in claim 19, including a substantially rigid, elongate sleeve removable coupled to said housing, said reservoir being secured to said sleeve.

* * * * *